(12) United States Patent
Kim

(10) Patent No.: US 9,334,513 B2
(45) Date of Patent: May 10, 2016

(54) METHOD FOR PRODUCING BIOLOGICAL HEME IRON, AND IRON SUPPLEMENTING COMPOSITION CONTAINING THE HEME IRON PRODUCED BY SAME

(75) Inventor: Pil Kim, Gyeonggi-Do (KR)

(73) Assignees: Catholic University Industry Academic Cooperation Foundation, Seoul (KR); iNtRON Biotechnology, Inc., Sungnam-Si (KR)

(*) Notice: Subject to any disclaimer, the term of this patent is extended or adjusted under 35 U.S.C. 154(b) by 431 days.

(21) Appl. No.: 13/063,669

(22) PCT Filed: Sep. 2, 2009

(86) PCT No.: PCT/KR2009/004946
§ 371 (c)(1),
(2), (4) Date: Apr. 27, 2011

(87) PCT Pub. No.: WO2010/030091
PCT Pub. Date: Mar. 18, 2010

(65) Prior Publication Data
US 2011/0213142 A1 Sep. 1, 2011

(30) Foreign Application Priority Data
Sep. 12, 2008 (KR) .................. 10-2008-0090482

(51) Int. Cl.
| | | |
|---|---|---|
| *C12Q 1/00* | (2006.01) | |
| *C12N 1/00* | (2006.01) | |
| *C12P 1/00* | (2006.01) | |
| *C12N 9/00* | (2006.01) | |
| *C12N 1/22* | (2006.01) | |
| *C12P 17/18* | (2006.01) | |
| *C07K 14/245* | (2006.01) | |
| *C12N 9/04* | (2006.01) | |
| *C12N 9/02* | (2006.01) | |
| *C12P 9/00* | (2006.01) | |
| *C12R 1/19* | (2006.01) | |

(52) U.S. Cl.
CPC ............. *C12P 17/182* (2013.01); *C07K 14/245* (2013.01); *C12N 9/0006* (2013.01); *C12N 9/0008* (2013.01); *C12P 9/00* (2013.01); *C12R 1/19* (2013.01); *Y02P 20/52* (2015.11)

(58) Field of Classification Search
None
See application file for complete search history.

(56) References Cited

FOREIGN PATENT DOCUMENTS

| JP | 2002193831 A | 7/2002 |
| KR | 20020085167 A | 11/2002 |

OTHER PUBLICATIONS

Hart et al. 1994 (Effect of biosynthetic manipulation of heme on insolubility of Vitreoscilla Hemoglobin in *Escherichia coli*; Appl. Env. Microb. 60(7):2431-2437).*
Kwon et al. 2008 (Iron associated hem-derivative biosynthesis from a metabolic engineered *Escherichia coli*; International symposium on Microbiology [S-10]; Daejeon Convention Center, Korea; May 15-16, 2008).*
Shin et al. 2006 (5-aminoevulinic acid biosynthesis in *Escherichia coli* co-expressing NADP-dependent malic enzyme and 5-aminolevulinate synthetase; J. Microbiol. Biotechnol. 17(9):1579-1584).*
Rieder 1970 (Hemoglobin Stability: Observations on the denaturation of normal and abnormal hemoglobins by oxidant dyses, heat and alkali; Journal of Clinical Investigation 49: 2369-2376).*
Kwon et al. 2003 (High-Level Production of Porphyrins in Metabolically Engineered *Escherichia coli*: Systematic Extension of a Pathway Assemebled from Overexpressed Genes Involved in Heme Synthesis; Appl. Environ. Microb. 69(8):4875-4883).*
Lee et al. 2013 (Effect of Gene Amplifications in Porphyrin Pathway on Heme Biosynthesis in a Recombinant *Escherichia coli*; J Microbiol. Biotechnol. 23(5) 668-673).*
Hayashi et al. 2006 (Highly accurate genome sequences of *Escherichia coli* K-12 strains MG1655 and W3110; Molecular Systems Biology, 2006: 1-5).*
Sorenson et al. 2005 (Advanced genetic strategies for recombinant protein expression in *Escherichia coli*; Journal of Biotechnology 115:113-128.*
Berry et al., Simultaneous determination of hemes a, band c from pyridine hemochrome spectra, Anal Biochem, 161(1):1-15 (1987).
DiIorio, Preparation of derivatives of ferrous and ferric hemoglobin, Methods Enzymol, 76:57-72 (1981).
Hart et al., Effect of Biosynthetic Manipulation of Heme on Insolubility of Vitreoscilla Hemoglobin in *Escherichia coli*, App. Environ. Microbiol., 60:2431-2437 (1994).
International Search Report for PCT/KR2009/004946 dated Apr. 6, 2010.
Kwon et al., Iron Associated Heme-Derivative Biosynthesis from a Metabolic Engineered *Escherichia coli*, 2008 International Symposium on Microbiology, [SIO-2], Daejeon Covention Center, Korea, May 15-16, 2008.
Olsson et al., In Vivo and In Vitro Studies of Bacillus subtilis Ferrochelatase Mutants Suggest Substrate Channeling in the Heme Biosynthesis Pathway, J. Bacteriol., 184:4018-4024 (2002).

(Continued)

*Primary Examiner* — Gary Nickol
*Assistant Examiner* — Mary Lyons
(74) *Attorney, Agent, or Firm* — Meunier Carlin & Curfman LLC

(57) ABSTRACT

The present invention relates to a method for biologically producing heme-iron through microorganism cultivation, and to an iron supplementing composition containing the heme-iron produced by the same. The present invention provides a method for biologically producing heme-iron through microorganism cultivation, making it possible to economically produce heme-iron or heme-iron preparations which can be safely used as an iron supplement.

8 Claims, 2 Drawing Sheets

(56) References Cited

OTHER PUBLICATIONS

Van Der Werf et al., 5-Aminolevulinate production by *Escherichia coli* containing the Rhodobacter sphaeroides hemA gene, Appl. Environ. Microbiol., 62:3560-2566 (1996).

Volkova et al., On the ortho-phenanthroline method of determination of iron in blood serum, Lab Delo, 2:97-98 (1967).

2008 International Symposium on Microbiology, [S10-2] (May 15, 2008).

* cited by examiner

METHOD FOR PRODUCING BIOLOGICAL HEME IRON, AND IRON SUPPLEMENTING COMPOSITION CONTAINING THE HEME IRON PRODUCED BY SAME

TECHNICAL FIELD

The present invention relates to a method for biologically producing heme-iron through microorganism cultivation, and to an iron supplementing composition containing the heme-iron produced by the same.

BACKGROUND ART

Iron (Fe) is a trace element that plays an important role as an essential component compositing hemoglobin, myoglobin, cytochrome, iron-sulfur protein, lactoferrin and various enzymes in human body. A normal adult male has approximately 4-5 g of iron in his body and 60% of it exists as a cofactor of hemoglobin in circulating red blood cells while 11% of it exists as iron enzymes that play an important role in metabolism. Another 15-25% is stored in the form of ferritin or hemosiderin.

Iron is not endogenously synthesized but is taken from food. Iron in food is classified into two forms, which are heme-iron and non heme-iron. In animal foods, 40% of the total iron content is heme-iron and the rest 60% of it is non heme-iron. In the meantime, iron included in vegetable foods is all non heme-iron. None of heme-iron has been reported as originated from microorganisms until today. The absorption efficiency of food iron varies greatly according to its form, either heme-iron or non heme-iron. For instance, the absorption rate of iron taken from animal foods is at least 10% and the absorption rate of iron from vegetable foods is 5% at best. In particular, the absorption of non heme-iron is affected by the degree of in vivo iron storage and other dietary factor such as the amount of ascorbic acid. Generally, a healthy adult absorbs only 5-10% of iron taken from foods. Therefore, iron deficiency is a very common nutritional issue over the world. To prevent or treat iron deficiency, iron compounds such as ferric chloride, ferric citrate, ferrous lactate and heme-iron are used as an iron supplements.

The advantage of such inorganic irons, the iron compounds, except heme-iron is that they have high iron content and are inexpensive. However, they demonstrate low in vivo absorption rate and might cause iron poisoning when over-taken. Therefore, heme-iron, the organic iron that shows high absorption rate with less side effects, is in increasing demand.

Heme-iron is largely included in hemoglobin and myoglobin, which is isolated from blood of slaughtered animal. There is a safety issue in using such heme-iron because of the risk of diseased animal, for example there is a chance that the slaughtered animal might have a disease such as bovine spongiform encephalopathy. Besides, iron content in hemoglobin is very low, so that over-taking is demanded, resulting in excessive taking of protein. Thus, it is still requested to develop a heme-iron preparation that is safe and efficient.

Heme-iron is a porphyrin complex containing iron atom. The biosynthesis pathway of heme-iron has been well studied. Heme-iron is known to be synthesized by the following pathway: cyclic tetrapyrrole ring is formed from eight 5-aminolevulinic acid (5-ALA); side chains are transformed; and then reduced iron is combined thereto. Therefore, 5-ALA is a crucial substrate for heme-iron biosynthesis. The present inventors have studied to design a method for biologically producing heme-iron by increasing intracellular 5-ALA production, leading to the completion of this invention that overcomes the problems of using heme-iron products originated from animal blood.

DISCLOSURE

Technical Problem

It is an object of the present invention to provide a method for biologically producing heme-iron through microorganism cultivation.

It is another object of the present invention to provide an iron supplementing composition containing the heme-iron produced by the same as an active ingredient.

It is a further object of the present invention to provide a microorganism producing heme-iron.

Technical Solution

To achieve the above objects, the present invention provides a method for biologically producing heme-iron which is characterized by the procedure comprising the step of cultivating a microorganism producing heme-iron and the step of recovering heme-iron from the culture solution and also characterized by the microorganism in which the activity of the enzymes involved in 5-ALA synthesis is increased or the expression of the said enzymes is up-regulated.

The method for biologically producing heme-iron of the present invention includes the step of cultivating a microorganism producing heme-iron. The cultivating step herein can be performed by the conventional microorganism culture method. The heme-iron preparations prepared by the method of the present invention become an active ingredient of an iron supplements that can be provided to human and animals.

In the method for biologically producing heme-iron of the present invention, the said microorganism can be any microorganism in which the activity of the enzymes involved in 5-ALA synthesis is increased or the expression of the said enzymes is up-regulated. The said microorganism can be isolated from the nature or developed by recombination or mutation.

In the present invention, "microorganism" indicates bacteria, yeast, fungi and animal or plant cells, but not always limited thereto.

In the present invention, "recombinant plasmid" indicates a plasmid containing a target gene operatively linked to an expression regulatory sequence so that it would be expressed when it is introduced into a host cell.

In the method for biologically producing heme-iron of the present invention, the said microorganism can be *E. coli* or yeast such as *Saccaromyces cerevisiae*.

Heme-iron is biosynthesized from 5-ALA through the pathway illustrated in FIG. 1. 5-ALA is synthesized from succinyl CoA and glycine through C4 pathway or from glutamate, NADPH and glutamyl tRNA through C5 pathway. In the biosynthesis of heme-iron, the synthesis of 5-ALA is the most crucial stage. So, it can be a way to increase the production of heme-iron by using a microorganism either with increasing the activity of the enzymes involved in 5-ALA synthesis or with enhancing the expression of the enzymes involved in 5-ALA synthesis.

In a preferred embodiment of the present invention, the said microorganism is characterized by the increase of the expression of one or more enzymes selected from the group consisting of 5-ALA synthase (HemA: SEQ. ID. NO: 7), dicarboxylic acid transporter (DctA: SEQ. ID. NO: 8) and NADP-dependent malic enzyme (MaeB: SEQ. ID. NO: 9).

In a preferred embodiment of the present invention, the said microorganism can be a recombinant microorganism transformed by a recombinant plasmid containing at least one of the genes encoding these HemA, MaeB and DctA.

In a preferred embodiment of the present invention, the said microorganism can be a recombinant microorganism over-expressing at least one of the three enzymes, comparing with the parent strain, which is either transformed by a recombinant plasmid containing all genes encoding HemA, MaeB and DctA or transformed simultaneously with each recombinant plasmid respectively containing each gene of HemA, MaeB and DctA.

In this invention, the "parent strain" indicates the original strain before being transformed by recombinant technique or mutation.

In a preferred embodiment of the present invention, the plasmid used for the transformation of the said microorganism can be a spontaneous expression plasmid. If such a spontaneous expression plasmid is used, the expensive inducing agent such as IPTG (isopropyl-β-D-thiogalactopyranoside) won't be necessary, which favors the mass-production of heme-iron.

In a preferred embodiment of the present invention, the spontaneous expression plasmid used for the transformation of the said microorganism can be derived from the pLex vector containing L-promoter of lamda phage.

In a preferred embodiment of the present invention, the said microorganism can be *E. coli* KCTC 18134P which is transformed by a recombinant plasmid containing the genes encoding HemA, MaeB, and DctA.

In the method for biologically producing heme-iron of the present invention, the said heme-iron can be microorganism culture solution containing heme-iron or the heme-iron preparations. According to the method of the invention, the microorganism culture solution contains heme-iron produced by the microorganism, so that it itself can be used as the heme-iron preparation providing heme-iron. Or heme-iron is further purified from the culture solution or cultured cells, which is used as the heme-iron preparations of the present invention.

In this invention, "heme-iron preparation" indicates the microorganism culture solution containing heme-iron produced by the microorganism or the heme-iron containing materials prepared from the said culture solution or the cultured cells.

The method for biologically producing heme-iron of the present invention contains the step of recovering heme-iron from the culture solution and/or the cultured cells. The heme-iron recovering step from the cultured cells consists of the following sub-steps: recovering microorganism from the culture solution; resuspending and disrupting the recovered microorganism; and obtaining the supernatant containing heme-iron from the lysate by centrifugation.

In the method for biologically producing heme-iron of the present invention, the step of recovering heme-iron from the culture solution and/or the said supernatant can additionally include the step of purifying heme-iron by heat-precipitation, extraction and freeze-dry.

In a preferred embodiment of the present invention, heme-iron can be obtained by extraction using acid-acetone.

The present invention also provides heme-iron preparations prepared from the culture solution of the heme-iron producing microorganism transformed by a recombinant plasmid containing at least one of the genes encoding HemA, MaeB and DctA.

In a preferred embodiment of the present invention, the said heme-iron producing microorganism can be a recombinant microorganism transformed by a recombinant plasmid containing the genes encoding HemA, MaeB and DctA.

In a preferred embodiment of the present invention, the said heme-iron producing microorganism can be a microorganism transformed by a spontaneous expression plasmid.

The present invention further provides heme-iron preparations produced by the method for biologically producing heme-iron and an iron supplementing composition containing the same as an active ingredient.

The heme-iron preparations of the present invention include heme-iron produced by the microorganism, so that they can be used as an iron supplement. According to a preferred embodiment of the present invention, the mouse provided with the heme-iron preparation prepared from the microorganism culture solution as an iron supplement demonstrated high blood heme content.

The present invention also provides a microorganism producing heme-iron in which the activity of the enzymes that are involved in 5-ALA synthesis is increased or the expression of the said enzymes is up-regulated.

In a preferred embodiment of the present invention, the said microorganism producing heme-iron is a recombinant microorganism transformed by a recombinant plasmid containing at least one of the genes encoding HemA, MaeB and DctA.

In a preferred embodiment of the present invention, the microorganism producing heme-iron can be the one over-expressing HemA, MaeB and DctA, comparing with the parent strain, by being transformed by a recombinant plasmid containing all genes encoding HemA, MaeB and DctA or by being transformed simultaneously with recombinant plasmids each containing the gene encoding HemA, MaeB and DctA respectively.

In a preferred embodiment of the present invention, the said recombinant plasmid can be a spontaneous expression plasmid.

In a preferred embodiment of the present invention, the said microorganism producing heme-iron can be *E. coli* or yeast, but not always limited thereto.

In a preferred embodiment of the present invention, the said microorganism producing heme-iron is *E. coli* KCTC 18134P.

Advantageous Effect

The present invention provides a method for biologically producing heme-iron through microorganism cultivation which makes it possible to economically produce heme-iron preparations which can be safely used as an iron supplement.

DESCRIPTION OF DRAWINGS

The application of the preferred embodiments of the present invention is best understood with reference to the accompanying drawings, wherein.

MODE FOR INVENTION

Figure 1:
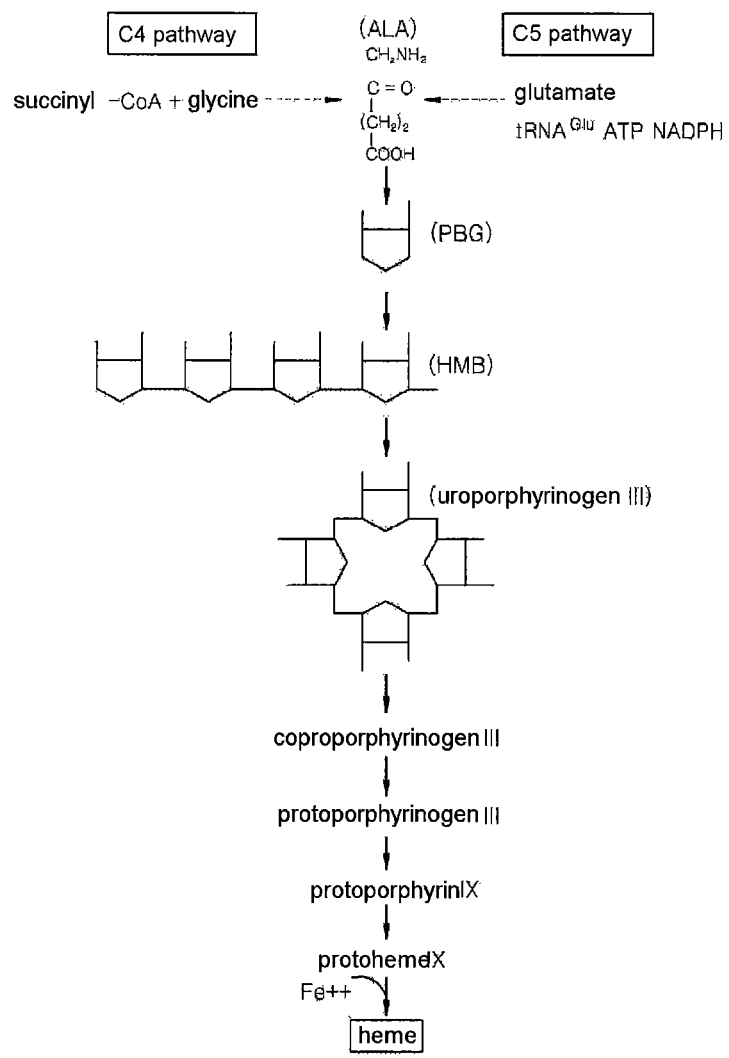
FIG. 1 is a diagram illustrating the biosynthesis pathway of heme-iron from 5-aminolevulinic acid (5-ALA).

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Heme-Iron Producing Recombinant *E. coli*

In this example, to increase the production of 5-ALA acting as a crucial substrate for heme-iron biosynthesis, recombinant *E. coli* was prepared by transforming with a plasmid containing the genes encoding the enzymes involved in 5-ALA synthesis, 5-ALA synthase (HemA), NADP-dependent malic enzyme (MaeB), and C4-dicarboxylic acid transporter protein (DctA).

(1) Construction of a Recombinant Plasmid Containing the Genes Encoding HemA, MaeB and DctA The sequence of *Rhodobacter sphaeroides* hemA gene (GenBank CP_000143, SEQ. ID. NO: 7), the sequence of HemA flanking region and the sequence of lac promoter were totally amplified by PCR using pALA7 (van der Werf, M. J. and J. G. Zeikus, 1996, Appl. Environ. Microbiol. 62: 3560-3566), which is derived from pUC19 and contains the sequence of HemA gene, the sequence of HemA flanking region and the sequence of lac promoter, as a template with primers represented by SEQ. ID. NO: 1 and NO: 2 (1 minute at 95° C., 1 minute at 55° C., 2 minutes at 72° C.; 25 cycles). The PCR product (2.0 kb) was inserted into TA-cloning vector (T&A Cloning Vector, RBC, Taiwan). Subsequently the target insert was sub-cloned from the TA-cloning product to pTrc99A (AP Biotech Co.) with XbaI and PstI, leading to the construction of pTrc($P_{lac}$hemA$^+$).

MaeB gene (Seq. ID. NO: 9) was amplified by PCR using genomic DNA (GenBank AC_000091) of *E. coli* W3110 (KCTC 2223) as a template with primers represented by SEQ. ID. NO: 3 and NO: 4 (1 minute at 95° C., 1 minute at 55° C., 2 minutes at 72° C.; 25 cycles). The PCR product (2.3 kb) was inserted into TA-cloning vector (T&A Cloning Vector, RBC, Taiwan). Subsequently the target insert was sub-cloned from the TA-cloning product to pTrc($P_{lac}$hemA$^+$) with PstI and HindIII, leading to the construction of pTrc($P_{lac}$hemA$^+$-maeB).

DctA gene (GenBank AC_000091:3956967.3958254: SEQ. ID. NO: 8) was amplified by PCR using genomic DNA (GenBank AC_000091) of *E. coli* W3110 (KCTC 2223) as a template with primers represented by SEQ. ID. NO: 5 and NO: 6 (1 minute at 95° C., 1 minute at 55° C., 2 minutes at 72° C.; 25 cycles). The PCR product (1.3 kb) was inserted into TA-cloning (T&A Cloning Vector, RBC, Taiwan). Subsequently the target insert was sub-cloned from the TA-cloning product to pTrc($P_{lac}$hemA$^+$-maeB) with HindIII, leading to the construction of pTrc($P_{lac}$hemA$^+$-maeB-dctA). The proper construction of recombinant plasmid was confirmed by the identification of DNA fragments (2.8 kb and 7.0 kb) generated by treating PstI and by sequencing (Solgent, Daejeon, Korea).

(2) Transformation with pTrc($P_{lac}$hemA$^+$-maeB-dctA)

*E. coli* W3110 was transformed with the pTrc($P_{lac}$hemA$^+$-maeB-dctA) constructed in Example 1(1) by electroporation (Gene Pulser, Bio-Rad, Hercules, Calif., U.S.A.), resulting in the construction of recombinant *E. coli* W3110/pTrc($P_{lac}$hemA$^+$-maeB-dctA) co-expressing HemA, MaeB and DctA altogether. As a control strain, *E. coli* W3110/pTrc99A was prepared by transforming *E. coli* W3110 with pTrc99A under the same conditions.

(3) Expression of HemA, MaeB and DctA

The recombinant *E. coli* W3110/pTrc($P_{lac}$hemA$^+$-maeB-dctA) cells and the control *E. coli* W3110/pTrc99A cells prepared in Example 1(2) were inoculated into medium S (5 g yeast extract, 10 g trypton, 5 g $KH_2PO_4$, 10 g succinate (disodium succinate hexahydrate), 2 g glycine, $FeCl_3$ 40 mg/L, pH 6.5) supplemented with ampicillin (20 µg/ml) and 0.1 mM IPTG, followed by culture in a rotary shaking incubator (37° C., 230 rpm) for 6 hours. The obtained culture solution was centrifuged at 4° C., at 3,000 g, for 15 minutes to recover cells. The recovered cells were suspended in 15 ml of distilled water, followed by disruption on ice for 1 minute using a sonicator (UP200S, Hielscher Ultrasonics GmbH, Teltow, Germany) set at 30 W at 1 second intervals. The cell lysate was centrifuged at 4° C., at 10,000 g, for 20 minutes. The expressed enzyme activity was measured using the cell lysate as follows. The amount of the enzyme producing 1 µmole/min of the product was determined as 1 unit. Quantification of the protein was performed with a BIO-Rad Protein Assay Kit using bovine serum albumin as a standard.

To measure the enzymatic activity of 5-ALA synthase (HemA), the incubation mixture (1 ml) composed of 50 mM Tris-HCl (pH 7.5), 20 mM $MgCl_2$, 0.1 M disodium succinate, 0.1 M glycine, 0.1 mM pyridoxal phosphate, 15 mM ATP, 0.2 mM CoA, and 50 µl of cell lysate was incubated at 37° C. for minutes. Then, $OD_{555}$ of the incubation mixture was measured by using a spectrophotometer (UV2450; Shimazu, Kyoto, Japan). The enzymatic activity of 5-ALA synthase of each the recombinant *E. coli* W3110/pTrc($P_{lac}$hemA$^+$-maeB-dctA) strain and the control *E. coli* W3110/pTrc99A strain was 1.22 unit/mg-protein and 0.01 unit/mg-protein respectively.

The enzymatic activity of NADP-dependent malic enzyme (MaeB) was determined by the NADPH level. The incubation mixture (1 ml) composed of 0.1 M Tris-HCl (pH 8.1), 20 mM $MnCl_2$, 2 mM $NH_4Cl$, 1 mM DTT, 1 mM $NADP^+$, 10 mM malate, 20 mM sodium arsenate, and 25 µl of cell lysate was incubated at 37° C. for 15 minutes. Then, $OD_{345}$ of the incubation mixture was measured by using a multi-plate spectrophotometer (Benchmark, Bio-Rad, Hercules, Calif., U.S.A.). Extinction coefficient of NADPH at 340 nm was 6.7 mM/cm. The enzymatic activity of NADP-dependent malic enzyme of each the recombinant *E. coli* W3110/pTrc($P_{lac}$hemA$^+$-maeB-dctA) strain and the control *E. coli* W3110/pTrc99A strain was 0.74 unit/mg-protein and 0.01 unit/mg-protein respectively.

The enzymatic activity of C4-dicarboxylic acid transporter (DctA) was measured by quantifying intracellular succinate with a 500 MHz FT-NMR spectrophotometer (UI1500; Varian Inc., Palo Alto, Calif., U.S.A.) in KBSI (Metabolome Analysis Facility, Korea Basic Science Institute Seoul Center). The cells recovered from the culture solution by centrifugation (12,000 rpm, 4° C., 10 minutes) were resuspended in 50 mM phosphate buffer (pH 7.0) containing 10 g/l disodium succinate hexahydrate. The prepared cell suspension stayed at room temperature for 1 minute to transfer succinate into the cells. Then, the cells were washed twice with distilled water to eliminate extracellular succinate. After resuspending the cells ($O.D_{600}$=1), 0.5 ml of the cell suspension was loaded in a 5-mm NMR tube, and mixed with 100 µl of $D_2O$ containing 0.75% TSP (trimethylsilyl-2,2,3,3-tetradeuteropropionic acid). Quantification was performed by conventional $^1$H-NMR. The amount of intracellular succinate of each the recombinant *E. coli* W3110/pTrc($P_{lac}$hemA$^+$-maeB-dctA) strain and the control *E. coli* W3110/pTrc99A strain was 14.6 µmol/OD cell and 1.8 µmol/OD cell respectively.

The above results indicate that the introduced HemA, MaeB and DctA were functionally expressed in the recombinant E. coli W3110/pTrc(P$_{lac}$hemA$^+$-maeB-dctA) strain.

The recombinant E. coli W3110/pTrc(P$_{lac}$hemA$^+$-maeB-dctA) strain constructed in this example was deposited at KRIBB (Korea Research Institute of Bioscience and Biotechnology) on Aug. 12, 2008 (Accession No. KCTC 18134P).

Example 2

Production of Heme-Iron Preparation Through Microorganism Cultivation

E. coli W3110/pTrc(P$_{lac}$hemA$^+$-maeB-dctA) transformed by pTrc(P$_{lac}$hemA$^+$-maeB-dctA) prepared in Example 1 was cultured to produce heme-iron extract.

(1) Cultivation of Recombinant E. coli

Single colony of the E. coli W3110/pTrc(P$_{lac}$hemA$^+$-maeB-dctA) strain was inoculated in 15-ml test tube containing 4 ml of LB (Luria-Bertani) medium (5 g yeast extract, 5 g NaCl, and 10 g bactotrypton per liter), followed by culture in a rotary shaking incubator (37° C., 230 rpm) for 16 hours. 1 ml of the culture solution was inoculated in 250 ml Erlenmeyer flask containing 50 ml of medium S (5 g yeast extract, 10 g trypton, 5 g KH$_2$PO$_4$, 10 g succinate (disodium succinate hexahydrate), 2 g glycine, FeCl$_3$ 40 mg per liter, pH 6.5) supplemented with ampicillin (20 μg/ml), followed by further culture for 4 hours. The resultant culture solution was inoculated in 5 L fermentor (Biotron, Bucheon, Korea) containing 3 L of medium S supplemented with ampicillin (20 μg/ml) and 0.1 mM IPTG. The culture solution in the fermentor was cultured for 38 hours (37° C., 0.5 vvm aeration, 300 rpm). The control E. coli W3110/pTrc99A strain prepared in Example 1 was also cultured under the same condition as that applied for the culture of the recombinant E. coli W3110/pTrc (P$_{lac}$hemA$^+$-maeB-dctA) strain.

Biomass was calculated by measuring OD$_{600}$. OD$_{600}$ was measured to calculate biomass, which was converted into dry cell weight (DCW) by using the coefficient of 1 O.D.=0.31 g/l. At 16$^{th}$ hour of culture, biomass of the control strain (E. coli W3110/pTrc99A) was increased to 0.44 g/l and biomass of the recombinant E. coli W3110/pTrc(P$_{lac}$hemA$^+$-maeB-dctA) strain was increased to 0.40 g/l. These biomass levels were maintained until the culture was terminated at 38$^{th}$ hour. Both the control and the recombinant E. coli culture solutions turned yellow after they were cultured for 16 hours. The color of the control E. coli culture solution was not changed after 16 hours of culture, but the color of the recombinant E. coli culture solution turned red over the time. The culture of the control and the recombinant E. coli strains were repeated twice.

2.6 g and 2.4 g of cells were recovered from 6 L of each the control and the recombinant E. coli culture solution (38 hours).

(2) Production of Heme-Iron Preparation

Each culture solution of the control and the recombinant E. coli obtained in Example 2(1) was centrifuged at 4° C. for 15 minutes at 3,000 rpm. Then, each resultant supernatant was used for the production of heme-iron preparation.

In addition, each recovered cells was washed twice with distilled water. The cells were suspended in 15 ml of distilled water, followed by disruption on ice for 20 minutes using a sonicator (UP200S, Hielscher Ultrasonics GmbH, Teltow, Germany) set at 30 W at 1 second intervals. Centrifugation was performed to eliminate cell debris at 4° C. for 10 minutes at 10,000 rpm. Each resultant supernatant was also used for the production of heme-iron preparation.

To prepare the heme-iron preparations, each supernatant was stored in a 65° C. water-bath for 30 minutes. Then, centrifugation was performed again at 4° C. for 10 minutes at 10,000 rpm to eliminate protein precipitates. The resultant supernatant was subjected to cold acid-acetone extraction.

Heme-iron, the red pigment, was extracted by cold acid-acetone extraction method (Di Iorio, E. E., Methods Enzymol, 1981. 76: p. 57-72). Each supernatant obtained above was loaded in 100 ml of acid-acetone (99.8 ml acetone+0.2 ml 10 N HCl) little by little with stirring at −20° C. The mixture was centrifuged at −20° C. for 30 minutes at 10,000 g. The said extraction procedure was repeated to eliminate red color completely from the precipitate. Each extracted solution with acid-acetone was neutralized by adding 10 N NaOH, and then evaporated by using a rotary evaporator. After evaporation, the remaining solution was freeze-dried to give the dried powder. The obtained dried powders were used as the heme-iron preparations in the subsequent experiments.

0.6 g of dried powder was obtained from the control and the recombinant E. coli culture solutions, respectively.

Protein content of the dried powder was quantified by using a BIO-Rad Protein Assay Kit (Bio-Rad, Hercules, Calif., U.S.A.) using bovine serum albumin as a standard. Iron amount was determined by ortho-phenanthroline colorimetry (Volkova, T. N. and N. V. Patrina, Lab Delo, 1967. 2: 97-8) using [Fe(NH$_4$)$_2$(SO$_4$)$_2$.6H$_2$O] as a standard. Heme amount was determined by colorimetry at 557 nm using hemin (Sigma, St. Louis, Mo., USA) as a standard.

As a result, the amount of heme measured from the recombinant and the control E. coli strains was respectively less than 64.0 mg/g-dried powder and 0.01 mg/g-dried powder. The amount of iron of each the recombinant and the control E. coli strains was respectively less than 6.8 mg/g-dried powder and 0.05 mg/g-dried powder. The cultivation results of the recombinant E. coli W3110/pTrc(P$_{lac}$hemA$^+$-maeB-dctA) and the control E. coli W3110/pTrc99A strains for the production of heme-iron were summarized in the below Table.

| Strain | Culture Solution | Cell Mass | Dried powder | Heme Amount | Iron Amount |
| --- | --- | --- | --- | --- | --- |
| E. coli W3110/pTrc99A | 6 L | 2.6 g | 0.6 g | <0.01 mg | <0.03 mg |
| E. coli W3110/pTrc (P$_{lac}$hemA$^+$-maeB-dctA) | 6 L | 2.4 g | 0.6 g | 38.4 mg | 4.1 mg |

(3) Confirmation of Heme-Iron

Figure 2:
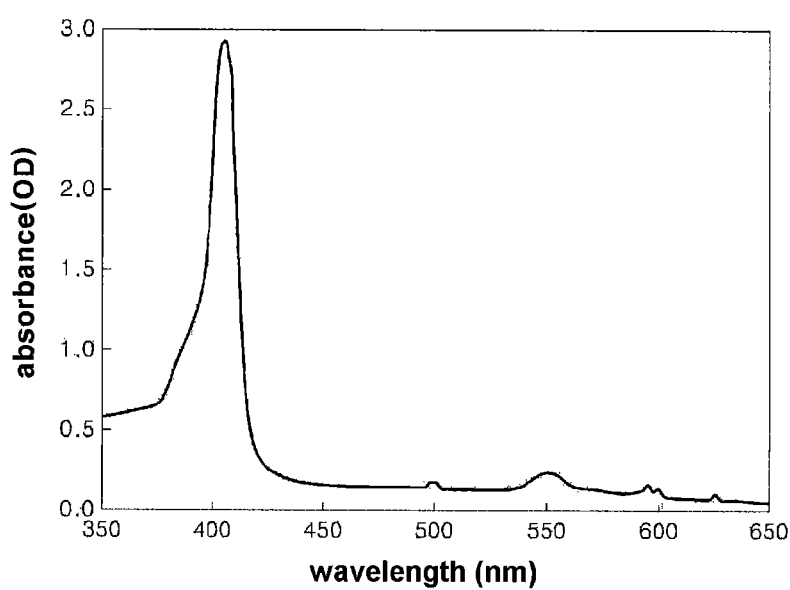
FIG. 2 is a graph illustrating the result of scanning the spectrum of the acid-acetone extract produced by the cultivation of the heme-iron producing microorganism according to one of examples of the present invention.

To confirm that the red color observed in the culture solution of the recombinant E. coli W3110/pTrc(P$_{lac}$hemA$^+$-maeB-dctA) strain was attributed to heme-iron, spectrum of the acid-acetone extract was analyzed by using a UV1240 spectrophotometer (Shimadzu, Kyoto, Japan). The spectrum of the acid-acetone extract (0.1 mg/ml) obtained from the recombinant E. coli strain showed its major peak at 407 nm and some minor peaks at 500, 551, 594, 599, and 625 nm, which were consistent with the characteristic spectrum of heme (Berry and Trumpower, Simultaneous determination of hemes a, b and c from_pyridine hemochrome spectra. Anal Biochem 161(1):1-15, 1987). FIG. 2 illustrates the spectrum of the acid-acetone extract comprising heme-iron produced from the culture of the recombinant E. coli strain. Therefore, it was confirmed that the red pigment produced in the culture solution of the recombinant E. coli strain was heme-iron.

Example 3

Use of Heme-Iron Preparation Produced by Microorganism Cultivation as an Iron Supplement In this example, the experiment was performed to confirm the possibility of using the heme-iron preparation produced by microorganism cultivation as an iron supplement.

21 female mice (ICR) at 12 weeks and iron-deficient feeds (AIN-93G) were purchased from Central Lab. Animal Inc. (Seoul, Korea). The weights of those mice were 32-34 g.

The mice were randomly divided into three groups (7 mice/group), to which iron-free feed pellet was supplied 6 g/day/mouse. The solution containing the heme-iron preparation (1 mg-dried heme-iron preparation powder in 0.5 ml) prepared in Example 2 was orally administered to group 1 mice every day using a 39 mm long round-head needle syringe. The solution containing the control dried powder (1 mg-dried powder in 0.5 ml) was orally administered to group 2 mice every day by the same method. Group 3 mice were treated with 0.5 ml distilled water every day. To prepare the control dried powder, the control E. coli W3110/pTrc99A strain was cultured under the same condition as described in Example 2. The dried powder was obtained by the same method used in the preparation of dried heme-iron preparation powder.

Feeding and excretion of those mice were observed every day for 15 days. Weights and feed consumption rates were measured once a week. Upon completion of the observation for 15 days, all the mice were sacrificed and blood was drawn by cardiac puncture. RBC content, packed RBC volume, hemoglobin content and heme content of the blood sample were measured with a hematocrit analyzer (MS9-5, Melet Schloesing Lab, Osny, France).

Severe weight changes were not observed in any of those three groups. Only about 2.3% weight loss was observed in group 3, but other groups scarcely showed weight changes. Group 1 mice showed the highest RBC level (9.8 cells/μl), the largest packed RBC volume (56.6%), and the highest hemoglobin level (15.5 g/dL). The most remarkable difference among these was blood heme level. Blood heme level of group 1 was 4.2 mg/ml, while group 2 and group 3 demonstrated 2.6 mg/ml and 2.5 mg/ml of blood heme levels, respectively.

Mice of group 1, group 2, and group 3, respectively treated with the solution containing dried heme-iron preparation powder prepared from the recombinant E. coli W3110/pTrc ($P_{lac}$hemA$^+$-maeB-dctA) strain culture solution, the solution containing dried powder prepared from the control E. coli W3110/pTrc99A strain culture solution, and distilled water, were raised for 15 days, and the results are shown in the below Table. Data is presented as mean±standard deviation. Statistic significance among the groups was determined by Student t-test. It was determined as significant when P<0.05.

| Mouse | Iron supplement | Weight after 15 days | Blood RBC (cells/mL) | Packed RBC volume (%) | Hemoglobin content (g/dL) | Heme content (mg/mL) |
|---|---|---|---|---|---|---|
| Group 1 | Solution containing dried powder prepared from the heme-iron producing strain culture solution | 99.8 ± 4.3 | 9.8 ± 0.2 | 56.6 ± 3.1 | 15.5 ± 0.7 | 4.2 ± 0.1 |
| Group 2 | Solution containing dried powder prepared from the control strain culture solution | 98.5 ± 3.7 | 8.7 ± 0.2 | 50.1 ± 2.8 | 13.9 ± 0.6 | 2.6 ± 0.1 |
| Group 3 | Water | 97.7 ± 4.2 | 9.2 ± 0.3 | 49.5 ± 4.2 | 14.5 ± 0.8 | 2.5 ± 0.2 |

The results of this example suggest that the heme-iron preparation prepared from the recombinant E. coli culture solution can be used as an iron supplement for animal.

All the research procedures related to this invention were performed according to the protocol approved by Catholic University Institutional Review Board.

Example 4

Construction of Heme-Iron Producing Strain Having Spontaneous Expression Plasmid To synthesis heme-iron by expressing HemA, MaeB and DctA in the recombinant E. coli W3110/pTrc($P_{lac}$hemA$^+$-maeB-dctA) constructed in Example 1, it is necessary to induce the gene group encoding HemA-MaeB-DctA which is involved in 5-ALA biosynthesis and regulated by trc promoter with IPTG. However, it is not easy to use IPTG in industrial production because of its high price. To overcome this problem, the said gene group (HemA-MaeB-DctA) was subcloned into pLex vector (3 kb, Invitrogen, Carlsbad, Calif., USA) containing lamda phage L promoter capable of inducing spontaneous expression in E. coli. The gene group was amplified by PCR using pTrc($P_{lac}$hemA$^+$-maeB-dctA) as a template with primers represented by SEQ. ID. NO: 10 and NO: 11 containing EcoRI and XbaI recognition sites respectively (1 minute at 94° C., 1 minute at 57° C., and 3 minutes at 72° C.; 30 cycles). The amplified 5.4 kb DNA fragment was inserted into T-vector (T&A cloning vector, RBC Co., Taiwan), followed by digestion with EcoRI-XbaI and ligation to pLex vector fragment prepared by digestion of the pLex vector with the same restriction enzymes previously. The proper construction of pLex-hemA⁺-maeB-dctA was confirmed by DNA sequencing and restriction enzyme mapping. Then, the constructed plasmid was introduced into *E. coli* W3110 by electroporation. The transformed W3110(pLex-hemA⁺-maeB-dctA) strain was cultured by the same manner as described in Example 2 except that IPTG-free medium S was used. Heme-iron level in the culture solution was measured and as a result it was confirmed that 6.2 mg/L (0.7 mg-iron/L) of heme-iron was produced.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for biologically producing heme-iron, comprising:

cultivating a heme-iron producing *Escherichia coli* W3110/pTrc($P_{lac}$hemA$^+$-maeB-dctA) in a medium consisting essentially of yeast extract, tryptone, $KH_2PO_4$, succinate, glycine, $FeCl_3$, wherein said *Escherichia coli* is transformed by a recombinant plasmid containing three genes encoding 5-aminolevulinic acid (5-ALA) synthase (HemA; SEQ. ID. NO: 7) originated from *Rhodobacter sphaeroides*, NADP-dependent malic enzyme (MaeB; SEQ. ID. NO: 9) originated from genomic DNA (GenBank AC_000091) of *Escherichia coli* W3110, and dicarboxylic acid transporter (DctA; SEQ. ID. NO: 8) originated from genomic DNA (GenBank AC_000091) of *Escherichia coli* W3110, is capable of co-expressing 5-ALA (5-aminolevulinic acid) synthase, NADP-dependent malic enzyme, and dicarboxylic acid transporter by induction, and whose accession number is KCTC 18134P;

adding IPTG (isopropyl-β-D-thiogalactopyranoside) to the culture of *Escherichia coli* W3110/pTrc($P_{lac}$hemA$^+$-maeB-dctA); and recovering heme-iron from a culture solution of said *Escherichia coli*.

2. The method for biologically producing heme-iron according to claim 1, wherein the step of recovering heme-iron comprises the following sub-steps:

recovering said *Escherichia coli* from the culture solution;
resuspending and disrupting said *Escherichia coli*; and
obtaining a supernatant containing heme-iron from a lysate by centrifugation.

3. The method for biologically producing heme-iron according to claim 2, wherein the step of recovering heme-iron additionally includes the step of purifying heme-iron from the supernatant by heat-precipitation or extraction.

4. A heme-iron producing *Escherichia coli* W3110/pTrc ($P_{lac}$hemA$^+$-maeB-dctA), wherein said *Escherichia coli* is transformed by a recombinant plasmid containing three genes encoding 5-aminolevulinic acid (5-ALA) synthase (HemA; SEQ. ID. NO: 7) originated from *Rhodobacter sphaeroides*, NADP-dependent malic enzyme (MaeB; SEQ. ID. NO: 9) originated from genomic DNA (GenBank AC_000091) of *Escherichia coli* W3110, and dicarboxylic acid transporter (DctA; SEQ. ID. NO: 8) originated from genomic DNA (GenBank AC_000091) of *Escherichia coli* W3110, is capable of co-expressing 5-ALA (5-aminolevulinic acid) synthase, NADP-dependent malic enzyme, and dicarboxylic acid transporter by induction, and whose accession number is KCTC 18134P.

5. A method for biologically producing heme-iron, comprising:

cultivating a heme-iron producing *Escherichia coli* W3110 (pLex-hemA$^+$-maeB-dctA), wherein said *Escherichia coli* is transformed in a medium consisting essentially of yeast extract, tryptone, $KH_2PO_4$, succinate, glycine, $FeCl_3$, wherein said *Escherichia coli* is transformed by a recombinant plasmid containing three genes encoding 5-aminolevulinic acid (5-ALA) synthase (HemA; SEQ. ID. NO: 7) originated from *Rhodobacter sphaeroides*, NADP-dependent malic enzyme (MaeB; SEQ. ID. NO: 9) originated from genomic DNA (GenBank AC_000091) of *Escherichia coli* W3110, and dicarboxylic acid transporter (DctA; SEQ. ID. NO: 8) originated from genomic DNA (GenBank AC_000091) of *Escherichia coli* W3110, is capable of spontaneous co-expression of 5-ALA (5-aminolevulinic acid) synthase, NADP-dependent malic enzyme and dicarboxylic acid transporter without induction; and recovering heme-iron from a culture solution of said microorganism.

6. The method for biologically producing heme-iron according to claim 5, wherein the step of recovering heme-iron comprises the following sub-steps:

recovering said *Escherichia coli* from the culture solution;
resuspending and disrupting said *Escherichia coli*; and
obtaining a supernatant containing heme-iron from a lysate by centrifugation.

7. The method for biologically producing heme-iron according to claim 6, wherein the step of recovering heme-iron additionally includes the step of purifying heme-iron from the supernatant by heat-precipitation or extraction.

8. A heme-iron producing *Escherichia coli* W3110(pLex-hemA$^+$-maeB-dctA), wherein said *Escherichia coli* is transformed by a recombinant plasmid containing three genes encoding 5-aminolevulinic acid (5-ALA) synthase (HemA; SEQ. ID. NO: 7) originated from *Rhodobacter sphaeroides*, NADP-dependent malic enzyme (MaeB; SEQ. ID. NO: 9) originated from genomic DNA (GenBank AC_000091) of *Escherichia coli* W3110, and dicarboxylic acid transporter (DctA; SEQ. ID. NO: 8) originated from genomic DNA (GenBank AC_000091) of *Escherichia coli* W3110, is capable of spontaneous co-expression of 5-ALA (5-aminolevulinic acid) synthase, NADP-dependent malic enzyme and dicarboxylic acid transporter without induction.

\* \* \* \* \*

```
                         SEQUENCE LISTING

<160> NUMBER OF SEQ ID NOS: 11

<210> SEQ ID NO 1
<211> LENGTH: 33
<212> TYPE: DNA
<213> ORGANISM: Artifical Sequence
<220> FEATURE:
<223> OTHER INFORMATION: forward primer for hemA

<400> SEQUENCE: 1
tctagacccc gcgcgttggc cgattcatta atg                          33

<210> SEQ ID NO 2
<211> LENGTH: 34
<212> TYPE: DNA
<213> ORGANISM: Artifical Sequence
<220> FEATURE:
<223> OTHER INFORMATION: reverse primer for hemA

<400> SEQUENCE: 2
ctgcagggat ccgccagcgg atcgcgcccc tcgc                         34

<210> SEQ ID NO 3
<211> LENGTH: 38
<212> TYPE: DNA
<213> ORGANISM: Artifical Sequence
<220> FEATURE:
<223> OTHER INFORMATION: forward primer for maeB

<400> SEQUENCE: 3
ctgcagagga ggaacagaca tggatgacca gttaaaac                     38

<210> SEQ ID NO 4
<211> LENGTH: 30
<212> TYPE: DNA
<213> ORGANISM: Artifical Sequence
<220> FEATURE:
<223> OTHER INFORMATION: reverse primer for maeB

<400> SEQUENCE: 4
aagcttttac agcggttggg tttgcgcttc                              30

<210> SEQ ID NO 5
<211> LENGTH: 41
<212> TYPE: DNA
<213> ORGANISM: Artifical Sequence
<220> FEATURE:
<223> OTHER INFORMATION: forward primer for dctA

<400> SEQUENCE: 5
aagcttagga ggaacagaca tgaaaacctc tctgcttttt a                 41

<210> SEQ ID NO 6
```

```
<211> LENGTH: 30
<212> TYPE: DNA
<213> ORGANISM: Artifical Sequence
<220> FEATURE:
<223> OTHER INFORMATION: reverse primer for dctA

<400> SEQUENCE: 6
aagcttttaa gaggataatt cgtgcgtttt                                        30

<210> SEQ ID NO 7
<211> LENGTH: 1224
<212> TYPE: DNA
<213> ORGANISM: Rhodobacter sphaeroides
<220> FEATURE:
<221> NAME/KEY: gene
<222> LOCATION: (1)..(1224)
<223> OTHER INFORMATION: hemA

<400> SEQUENCE: 7
tcaggcaacg acctcggcgc gattcagcgc acagtgctgc cagagcacgt ccatggcctt       60
cacgaggtga tcgatcatgc cggaatcatg cacgggcgac ggggtgaagc gcagccgctc      120
ggtcccgcgc ggcacggtcg ggaagttgat cggctggaca tagatgccga aatgctcgag      180
cagcatgtcc gagatcatct tgcagtgcac ggggtcgccc acatggaccg gcacgatgtg      240
cgagccgtgg tcgatgatcg gcaggccgag ccccttgagg cgcatcttca ggatgcgggc      300
ctgggtctgg tgcttctcgc gcagctccac atcgcccttg aggtggcgca ccgaggccgc      360
cgcaccggcc gccacgacgg gcggcagcga ggtcgagaag atgaagcccg gcgcgtagga      420
gcgcaccgcg tcgcacatct ttgacgaggc gcgatatag ccgccgaaca cgccataggc       480
cttgcccagc gtcccgttga tgatgtcgat ccggtccatc agcccgtccc gctcggccac      540
gccgccgccg cggggggccgt acatgccgac ggcatggacc tcgtcgatgt atttcagcgc    600
gccgaactcg tcggcgatgt cgcagatctc ctcgatgcgg ccgaagtcgc catccatcga     660
atagacggat tcgaaggcca cgaggatcgg acggtccttg ccgatcgagg tcaggatccg     720
gcgcaggtcg tcgaggtcat tgtgcttgaa gatgtgcttc tcggtgcccg agcggcggat    780
gccctcgatc atcgaagcgt ggttcaactt gtccgagacg atgacgaggc ccgggatcag    840
ctgcggcagc gtcgagaggg tcgcgtcgtt ggcgatatag gccgacgaga agaccagcgc    900
cgcttccttg ccgtgcaggt cggcgagctc ggcctcgagg cgcttgtgat agagcgtggt    960
gcccgagatg ttgcgcgtgc cgcccgaccc ggcgccggtc gaatccagcg cctcgtgcat   1020
ggcccccagc accaccggat gctggcccat gccgagatag tcgttgccgc accagacggt  1080
gatttccttc tcgctcccgt cgggcttgcg ccacatggct ttcgggaagg cacccttgcg  1140
ccgctcgatg tcgatgaagg tccggtaccg gccctcggta tggagccggt tcagagcggt  1200
atcgagtgcc agattgtagt ccat                                            1224

<210> SEQ ID NO 8
<211> LENGTH: 1287
<212> TYPE: DNA
<213> ORGANISM: Escherichia coli
<220> FEATURE:
<221> NAME/KEY: gene
<222> LOCATION: (1)..(1287)
<223> OTHER INFORMATION: dctA

<400> SEQUENCE: 8
atgaaaacct ctctgtttaa aagcctttac tttcaggtcc tgacagcgat agccattggt       60
attctccttg gccatttcta tcctgaaata ggcgagcaaa tgaaaccgct tggcgacggc      120
```

```
ttcgttaagc tcattaagat gatcatcgct cctgtcatct tttgtaccgt cgtaacgggc      180
attgcgggca tggaaagcat gaaggcggtc ggtcgtaccg gcgcagtcgc actgctttac      240
tttgaaattg tcagtaccat cgcgctgatt attggtctta tcatcgttaa cgtcgtgcag      300
cctggtgccg aatgaacgt cgatccggca acgcttgatg cgaaagcggt agcggtttac       360
gccgatcagg cgaaagacca gggcattgtc gccttcatta tggatgtcat cccggcgagc      420
gtcattggcg catttgccag cggtaacatt ctgcaggtgc tgctgtttgc cgtactgttt      480
ggttttgcgc tccaccgtct gggcagcaaa ggccaactga ttttaacgt catcgaaagt       540 ttctcgcagg tcatcttcgg catcatcaat atgatcatgc gtctggcacc tattggtgcg      600
ttcggggcaa tggcgtttac catcggtaaa tacggcgtcg gcacactggt gcaactgggg      660
cagctgatta tctgtttcta cattacctgt atcctgtttg tggtgctggt attgggttca      720
atcgctaaag cgactggttt cagtatcttc aaatttatcc gctacatccg tgaagaactg      780
ctgattgtac tggggacttc atcttccgag tcggcgctgc cgcgtatgct cgacaagatg      840
gagaaactcg gctgccgtaa atcggtggtg gggctggtca tcccgacagg ctactcgttt      900
aaccttgatg gcacatcgat atacctgaca atggcggcgg tgtttatcgc ccaggccact      960
aacagtcaga tggatatcgt ccaccaaatc acgctgttaa tcgtgttgct gctttcttct     1020
aaaggggcgg cagggagtaac gggtagtggc tttatcgtgc tggcggcgac gctctctgcg     1080
gtgggccatt tgccggtagc gggtctggcg ctgatcctcg gtatcgaccg ctttatgtca     1140
gaagctcgtg cgctgactaa cctggtcggt aacggcgtag cgaccattgt cgttgctaag     1200
tgggtgaaag aactggacca caaaaaactg gacgatgtgc tgaataatcg tgcgccggat     1260
ggcaaaacgc acgaattatc ctcttaa                                         1287

<210> SEQ ID NO 9
<211> LENGTH: 2280
<212> TYPE: DNA
<213> ORGANISM: Escherichia coli
<220> FEATURE:
<221> NAME/KEY: gene
<222> LOCATION: (1)..(2280)
<223> OTHER INFORMATION: maeB

<400> SEQUENCE: 9
ttacagcggt tgggtttgcg cttctaccac ggccagcgcc accatgttga cgatacgacg       60
caccgatgcg atcggcgtta acacgtgaac cggtttcgcc acacccatca gcaccgggcc      120
gacagtcaca ccttccgagc tggaaacacg cagtaagttg taactaatgc gggcagcttc      180
catgttcggc atcaccagaa tattggcgga acctttcaaa gagctgtccg catacggtc       240 gttgcgaatc gcttccacca cgctgcatc gccgtgcatt tcaccatcaa tcatcagttc       300
tggtgcacgt tccctgacca gttccagcgc ctgacgcatt ttgctcgacg acgggcagtc      360
agaagaacca agttggagt gcgacaacaa agcaacgcgc ggctcaatac caaaacgacg       420
gacagtttct gccgccatca aggtgatctc cgccagctct tctgcatccg gttcatcatt      480
aacatatgta tcggcaataa aggtgttacc actcggcagc agcagcgcgt tcatggcacc      540
tgcggtgtga acgccatcgc gataaccaaa gacattttc accacgctaa atgttcatg       600 ataatcaccc accgtaccgc aaatcattgc atcggcttcc ccacgctgaa ccatgatcgc      660
gccgatcact gtcgggttac tgatcagcgc ccgctgcgcc tgttcctgag tgacgccgcg      720
acgcttcatg atctggaagt attcggtcca gtactcttta aagcgcggat cggattcgtt      780
```

```
attgacgatc tcaaaatcaa cgcccgcttt gatctgcaag cccagtttct gaatgcgcat    840
ttcgatcacg ttcggacgac cgataaggat cggtttcgcc agtcccagcg ttaccagttc    900
ctgagtggca tgcagaacgc gcgcctcttc cccttccggc agaacaacgc gcttcggcgc    960
tttgcgagcc tgggagaaaa tcggcttcat aaacaggttg gttttgtaaa cgaactcagt   1020
cagcttgtcg atgtagacgt cgaaatcagc aatcggacga gtcgccacgc ccgactccat   1080
cgcggcttta gcgaccgcag gagcgatctt aacgatcaag cgcggatcaa acggttttgg   1140
aatgatgtat tccggaccaa agctcagatc ctgatcgcca tacgctgaag ccaccacttc   1200
gctctgttcc gcatgggcga gttctgcaat cgcacgtacc gccgccagtt tcatctcttc   1260
gttgatggcg gttgcgccaa cgtccagcgc gccacggaag atgaacggga agcacaggac   1320
gttgttcacc tggttcggat agtcagaacg accggtgcaa atgatggcat ccggacgcac   1380
ttctttcgcc agcggcggca gaatttccgg ttccgggttc gccagcgcca ggatcattgg   1440
cgcacgagcc attttcttca ccatttcctg ggtcagcact tcgggccgg aacagcccag    1500 gaaaatatcc gcgccttcaa tcacatcatc gagggtacgt ttgccgtcat ccaccaccgc   1560
atatgcggct ttggtttccg ccatgtttgg ctcacggccc tgatagataa cgccttttga   1620
atcgcaaacc acgatgttat gtttttgcag acccagcgct accagcaggt tcatacaggc   1680
gattgctgcg gcacccgcgc cggaaaccac catccgcacg tcggagatgt ttttctccac   1740
cacgcgcaag ccgttgagga tggcggcagt gctgataatt gccgtgccgt gctgatcgtc   1800
gtggaatacc ggaatattca tccgctcgcg cagtttctgt tcaatataga acattctgg    1860 cgctttaatg tcttcgaggt tgatgccgcc gaaggttggt tcgagcgcgg cgacaacttc   1920
aataaatttg tccgggtcga gttcgtcaac ttcaatgtca aatacatcaa tcccggcgaa   1980
tttcttaaac agaacgccct tgccttccat caccggtttg cctgccagcg cgccaatgtt   2040 gcctaaccccc agcaccgccg taccgttaga gatcaccgcc accaggttac ctcgggcggt   2100
atatttgtag gcttttaacg ggtcttttttc gatttcaaga caaggtgcgg caacgcctgg   2160
tgagtaggcc agcgccagat cgcgctgtgt tgccagaggc ttggttggag aaacctggat   2220
tttccctgga actggaaatt catggaaatc aagtgcactt tgttttaact ggtcatccat   2280
```

<210> SEQ ID NO 10
<211> LENGTH: 27
<212> TYPE: DNA
<213> ORGANISM: Artifical Sequence
<220> FEATURE:
<223> OTHER INFORMATION: forward primer for hemA-maeB-dctA

<400> SEQUENCE: 10
gaattcatgg actacaatct ggcactc                                         27

<210> SEQ ID NO 11
<211> LENGTH: 28
<212> TYPE: DNA
<213> ORGANISM: Artifical Sequence
<220> FEATURE:
<223> OTHER INFORMATION: reverse primer for hemA-maeB-dctA

<400> SEQUENCE: 11
tctagattaa gaggataatt cgtgcgtt                                        28